United States Patent
Anklesaria (10) Patent No.: US 9,147,333 B1
(45) Date of Patent: Sep. 29, 2015

(54) REMOTE CONTROLLED DETECTION SYSTEM

(71) Applicant: Kaiomars P. Anklesaria, Bloomingdale, GA (US)

(72) Inventor: Kaiomars P. Anklesaria, Bloomingdale, GA (US)

(73) Assignee: Enuresis Solutions LLC, Savannah, GA (US)

( * ) Notice: Subject to any disclaimer, the term of this patent is extended or adjusted under 35 U.S.C. 154(b) by 24 days.

(21) Appl. No.: 14/146,160

(22) Filed: Jan. 2, 2014

(51) Int. Cl.
*G08B 21/00* (2006.01)
*G08B 21/18* (2006.01)
*G08B 25/14* (2006.01)
*G08B 25/10* (2006.01)

(52) U.S. Cl.
CPC .............. *G08B 21/182* (2013.01); *G08B 21/00* (2013.01); *G08B 25/10* (2013.01); *G08B 25/14* (2013.01)

(58) Field of Classification Search
CPC .......... G08B 21/00; G08B 3/10; G08B 25/14; G08B 25/10; G08B 13/1436; G08B 19/00
USPC .......... 340/515, 426.25, 5.23, 568.6, 426.17, 340/426.16, 573.1, 545.1, 539.21, 5.72, 340/506, 539.1, 539.19
See application file for complete search history.

(56) References Cited

U.S. PATENT DOCUMENTS

| | | | | |
|---|---|---|---|---|
| 5,260,689 | A * | 11/1993 | Meyers et al. | 340/568.6 |
| 2004/0113778 | A1* | 6/2004 | Script et al. | 340/545.1 |
| 2005/0030179 | A1* | 2/2005 | Script et al. | 340/545.1 |
| 2006/0097868 | A1* | 5/2006 | Ingram et al. | 340/571 |
| 2006/0176167 | A1* | 8/2006 | Dohrmann | 340/506 |
| 2007/0194923 | A1* | 8/2007 | Karr | 340/572.1 |
| 2007/0265009 | A1* | 11/2007 | Hamaguchi | 455/436 |
| 2009/0128323 | A1* | 5/2009 | Milbar | 340/539.1 |
| 2012/0194353 | A1* | 8/2012 | Groves | 340/907 |
| 2012/0206265 | A1* | 8/2012 | Solazzo et al. | 340/573.5 |
| 2013/0110064 | A1* | 5/2013 | Richardson et al. | 604/361 |
| 2013/0229278 | A1* | 9/2013 | Davis | 340/521 |
| 2014/0253326 | A1* | 9/2014 | Cho et al. | 340/539.13 |

* cited by examiner

*Primary Examiner* — Hoi Lau
(74) *Attorney, Agent, or Firm* — G. Brian Pingel; David M. Breiner (57) ABSTRACT

In accordance with example embodiments, a system may include a sensor, a remote, and one or more transceivers. In example embodiments, the sensor may be configured to sense a condition and send a first signal when the condition is sensed. In example embodiments, the first signal includes a first unique identifier. In example embodiments, the remote is configured to send a second and third signal (for remote "on" and "off") and the second and third signals will include a second unique identifier. In example embodiments, the first transceiver is configured to receive and retransmit the first, second and third signals.

A retransmission of the third signal from the remote further deactivates the transceiver(s) from the "ready" state to the "off" state. Sending the second signal from the remote (the "on" signal) resets the transceiver(s) from the "off" state to the "ready" state.

9 Claims, 6 Drawing Sheets

REMOTE CONTROLLED DETECTION SYSTEM

BACKGROUND

1. Field

Example embodiments relate to a detection system. In example embodiments the detection system may be used to for multiple purposes including, but not limited to, detecting a bodily fluid.

2. Description of the Related Art

Nocturnal enuresis, commonly called bedwetting, is a common childhood urologic complaint. Nocturnal enuresis is also common among adults who, for one reason or another, have reduced bladder control. Common treatments available for nocturnal enuresis include medication and bedwetting alarm systems.

In the conventional art, bedwetting alarm systems are normally comprised of a urine detector, often arranged in a person's undergarments, and an alarm that may be clipped to an article of clothing the person is wearing, or an alarm beside the patient or caregiver which is switched on by a wireless signal from the detector. In the conventional art, the person wearing the bedwetting alarm system may fall asleep. If the urine detector detects the presence of urine while the person is sleeping, the alarm may generate a noise or a vibration to wake the person up.

SUMMARY

Example embodiments relate to a detection system. In example embodiments the detection system may be used to for multiple purposes including, but not limited to, detecting a bodily fluid.

In accordance with example embodiments, a system may include a sensor, a transceiver, and a remote. In example embodiments, the sensor may be configured to sense a condition and send a first signal when the condition is sensed. In example embodiments, the first signal may include a first unique identifier. In example embodiments, the remote may be configured to send a second signal and the second signal may include a second unique identifier. In example embodiments, the first transceiver may be configured to receive and retransmit the first and second signals. In example embodiments the first transceiver may be configured to activate a first alarm when the first signal is received and deactivate the first alarm when the second signal is received.

BRIEF DESCRIPTION OF THE DRAWINGS

Example embodiments are described in detail below with reference to the attached drawing figures, wherein.

DETAILED DESCRIPTION

Example embodiments will now be described more fully with reference to the accompanying drawings, in which example embodiments of the invention are shown. The invention may, however, be embodied in different forms and should not be construed as limited to the example embodiments set forth herein. Rather, these example embodiments are provided so that this disclosure will be thorough and complete, and will fully convey the scope of the invention to those skilled in the art. In the drawings, the sizes of components may be exaggerated for clarity.

In this application, it is understood that when an element or layer is referred to as being "on," "attached to," "connected to," or "coupled to" another element or layer, it can be directly on, directly attached to, directly connected to, or directly coupled to the other element or layer or intervening elements that may be present. In contrast, when an element is referred to as being "directly on," "directly attached to," "directly connected to," or "directly coupled to" another element, there are no intervening elements present. As used herein, the term "and/or" includes any and all combinations of one or more of the associated listed items.

In this application it is understood that, although the terms first, second, etc. may be used herein to describe various elements and/or components, these elements and/or components should not be limited by these terms. These terms are only used to distinguish one element, component, region, layer, and/or section from another elements, component, region, layer, and/or section. Thus, a first element, component region, layer or section discussed below could be termed a second element, component, region, layer, or section without departing from the teachings of example embodiments.

Spatially relative terms, such as "beneath," "below," "lower," "above," "upper," and the like, may be used herein for ease of description to describe one element or feature's relationship to another element(s) or feature(s) as illustrated in the figures. It will be understood that the spatially relative terms are intended to encompass different orientations of the structure in use or operation in addition to the orientation depicted in the figures. For example, if the structure in the figures is turned over, elements described as "below" or "beneath" other elements or features would then be oriented "above" the other elements or features. Thus, the exemplary term "below" can encompass both an orientation of above and below. The structure may be otherwise oriented (rotated 90 degrees or at other orientations) and the spatially relative descriptors used herein interpreted accordingly.

Embodiments described herein will refer to planform views and/or cross-sectional views by way of ideal schematic views. Accordingly, the views may be modified depending on manufacturing technologies and/or tolerances. Therefore, example embodiments are not limited to those shown in the views, but include modifications in configurations formed on the basis of manufacturing process. Therefore, regions exemplified in the figures have schematic properties and shapes of regions shown in the figures exemplify specific shapes or regions of elements, and do not limit example embodiments.

The subject matter of example embodiments, as disclosed herein, is described with specificity to meet statutory requirements. However, the description itself is not intended to limit the scope of this patent. Rather, the inventors have contemplated that the claimed subject matter might also be embodied in other ways, to include different features or combinations of features similar to the ones described in this document, in conjunction with other technologies. Generally, example embodiments relate to a detection system. In example embodiments the detection system may be used to for multiple purposes including, but not limited to, detecting a bodily fluid.

Figure 1:
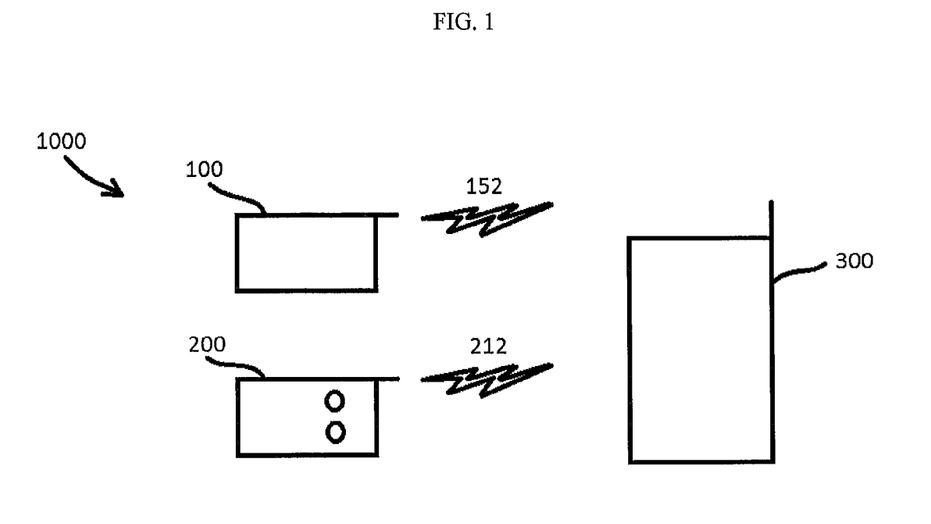
FIG. 1 is a view of a system in accordance with example embodiments.

FIG. 1 is a block diagram of a system 1000 in accordance with example embodiments. As shown in FIG. 1, the system 1000 may include a sensor 100, a remote 200, and a transceiver 300. In example embodiments, each of the sensor 100 and the remote 200 may be configured to generate a signal and the transceiver 300 may be configured to receive and retransmit the signals received from the sensor 100 and the remote 200. For example, in example embodiments, the sensor 100 may be configured to generate a first signal 152 and the remote 200 may be configured to generate a second signal 212, and a third signal 213. In example embodiments, the transceiver 300 may be attached to auxiliary equipment that may be configured to generate a noise, a light, a vibration, or a combination thereof. For example, the transceiver 300 may be connected to a bed shaker which may be configured to shake a bed, an alarm which may generate a noise, and/or a light which may turn on under the influence of the transceiver 300.

Figure 2A:
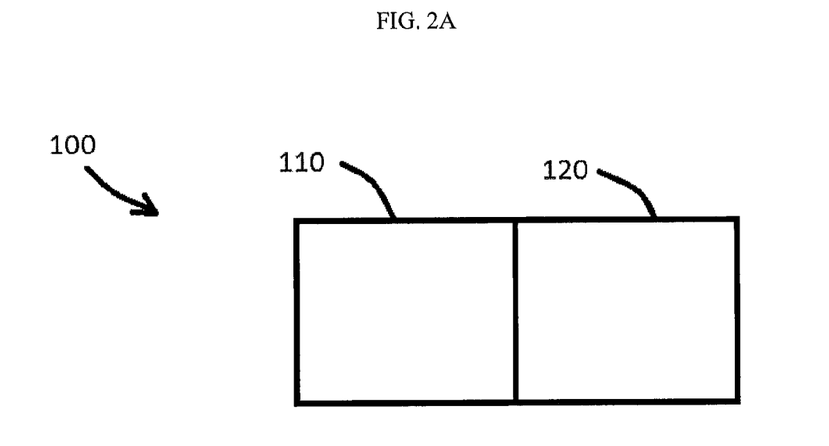
FIG. 2A is a schematic view of a sensor in accordance with example embodiments.

FIG. 2A is a block diagram of the sensor 100 in accordance with example embodiments. As shown in FIG. 2A, the sensor 100 may include a sensing unit 110 and a signal generator/transmitter unit 120. In example embodiments, the sensing unit 110 may be configured to sense a condition and the signal generator/transmitter unit 120 may be configured to generate and transmit a signal based on a condition sensed by the sensing unit 110. For example, in example embodiments, the sensing unit 100 may be configured to sense a condition, such as, but not limited to, a temperature, a pressure, a humidity, and/or a wetness. In the alternative, the sensing unit 110 may be configured to sense a chemical compound such as, but not limited to, carbon monoxide. Thus, the signal generator/transmitter unit 120 may also be configured to generate and transmit a signal based on a presence of a chemical compound sensed by the sensing unit 110. In the alternative, the sensing unit 110 may be configured to detect other items such as, but not limited to, smoke or even bodily fluids. Thus, the signal generator/transmitter unit 120 may also be configured to generate and transmit a signal based on a presence of other items, such as, but not limited to, a sensed smoke or a sensed bodily fluid.

In example embodiments the signal generator/transmitter 120 may generate and/or transmit the signal 152 in the event the sensing unit 110 senses anyone of the aforementioned conditions and/or items. In example embodiments the signal 152 may be sent over a wire or may be sent wirelessly. In example embodiments, a first signal identifier may be embedded in the first signal 152 and the first signal identifier may be, but is not required to be, a unique signal identifier.

Figure 2B:
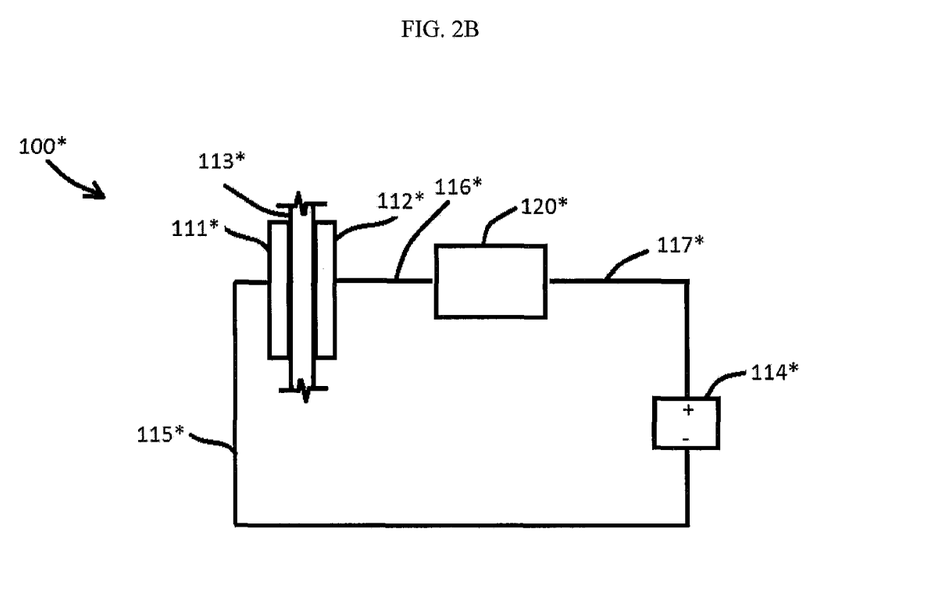
FIG. 2B is a schematic view of a sensor in accordance with example embodiments.

FIG. 2B is an example of a sensor 100* (which may be similar or identical to the sensor 100) in accordance with example embodiments. As shown in FIG. 2B, the sensor 100* may include a first electrode 111* and a second electrode 112* separated by an electrically insulating material 113*. For example, each of the first and second electrodes 111* and 112* may be separated by material associated with a wrapping or an article of clothing such as, but not limited to, a gauze bandage or an undergarment, for example, cotton briefs.

In example embodiments the sensor 100* may also include a power source 114*. The power source 114*, for example, may be a battery such as, but not limited to, a three volt battery. Example embodiments, however, are not limited to a sensor 100 having a three volt battery as a power source 114*. For example, the power source 114* may have a different voltage or may be an AC power source. In example embodiments, a first wire 115* may connect the power source 114* to the first electrode 111*, a second wire 116* may connect the second electrode 112* to a signal generator/transmitter 120*, and a third wire 117*, may connect the signal generator/transmitter 120* to the power source 114*. Thus, in example embodiments, the first wire 115*, the second wire 116*, the third wire 117*, the first electrode 111*, the second electrode 112* and the power source 114* may form an electrical circuit through which current may flow.

In example embodiments, the insulating material 113* may be comprised of an absorbent material. For example, as mentioned above, the insulating material 113* may be a cotton type material and thus may be capable of absorbing human body fluid such as, but not limited to, blood and urine. Thus, in example embodiments, if the insulating material 113* is dry, the insulating material 113* may prevent an electrical current from flowing from the first electrode 111* to the second electrode 112*. Thus an electrical open circuit is created so that no electrical current flows through it. However, in the event the insulating material 113* is exposed to a body fluid such as, but not limited to, blood and/or urine, electrolytes in the body fluid may allow an electrical current to flow from the first electrode 111* to the second electrode 112*. Accordingly, when the insulating material 113* is subjected to a body fluid, an electrical current may flow from the power source 114*, through the first wire 115*, through the first electrode 111*, through the insulating material 113*, through the second electrode 112*, through the second wire 116*, through the signal generator/transmitter 120*, through the third wire 117* and back to the power source 114*. In example embodiments, the electrical current flowing through the signal generator/transmitter 120* may power the signal generator/transmitter 120* so that the signal generator/transmitter 120* produces and transmits the first signal 152.

Figure 2C:
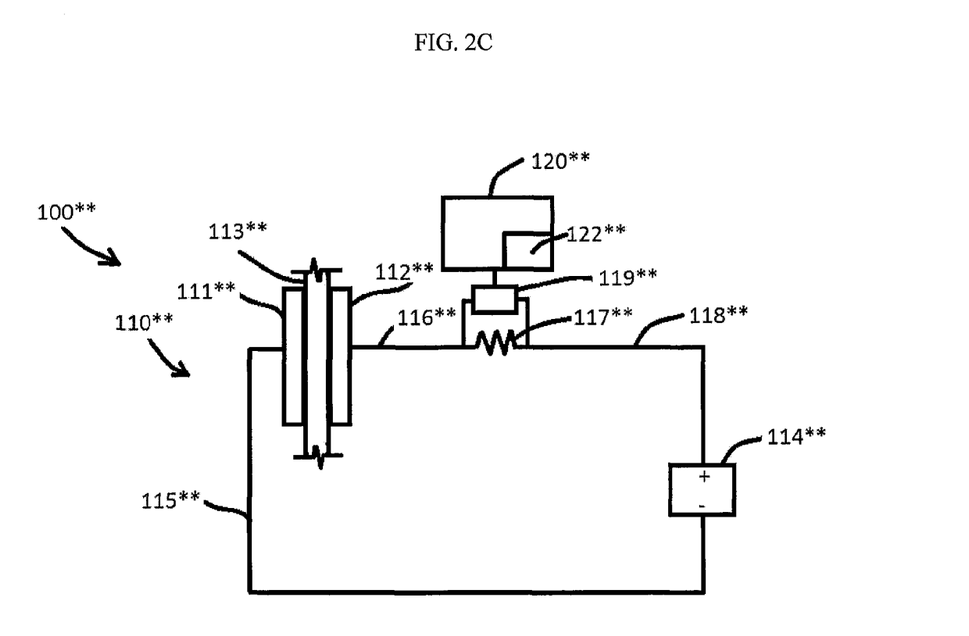
FIG. 2C is a schematic view of a sensor in accordance with example embodiments.

FIG. 2C is another example of a sensor 100 (which may be similar or identical to the sensor 100) in accordance with example embodiments. As shown in FIG. 2C, the sensor 100 may include a first electrode 111 and a second electrode 112 separated by an electrically insulating material 113. For example, each of the first and second electrodes 111 and 112 may be separated by material associated with a wrapping or an article of clothing such as, but not limited to, a gauze bandage or an undergarment, for example, cotton briefs.

In example embodiments the sensor 100 may also include a power source 114. The power source 114, for example, may be a battery such as, but not limited to, a three volt battery. Example embodiments, however, are not limited to a sensor 100 having a three volt battery as a power source 114. For example, the power source 114 may have a different voltage or may be an AC power source. In example embodiments, a first wire 115 may connect the power source 114 to the first electrode 111", a second wire 116 may connect the second electrode 112 to a resister 117, and a third wire 118, may connect the resister 117 to the power source 114. Thus, in example embodiments, the first wire 115, the second wire 116, the third wire 118, the first electrode 111, the second electrode 112 and the resister 117** may form an electrical circuit through which current may flow.

In example embodiments, the insulating material 113 may be comprised of an absorbent material. For example, as mentioned above, the insulating material 113 may be a cotton type material and thus may be capable of absorbing human body fluid such as, but not limited to, blood and urine. Thus, in example embodiments, if the insulating material 113 is dry, the insulating material 113 may prevent an electrical current from flowing from the first electrode 111 to the second electrode 112. However, in the event the insulating material 113 is exposed to a body fluid such as, but not limited to, blood and/or urine, electrolytes in the body fluid may allow an electrical current to flow from the first electrode 111 to the second electrode 112. Accordingly, when the insulating material 113 is subjected to a body fluid, an electrical current may flow from the power source 114, through the first wire 115, through the first electrode 111, through the insulating material 113, through the second electrode 112, through the second wire 116, through the resister 117, through the third wire 118 and back to the power source 114**.

In example embodiments, the sensor 100 may further include a voltage detector 119 operatively connected to a signal generator/transmitter 120. In example embodiments the voltage detector 119 may be configured to determine whether there is a voltage drop or increase across the resister 117. Such a voltage drop or increase across 117 may occur when current is flowing through the resister 117** and may happen, for example, when the insulating material 113* is an absorbent material having bodily fluids absorbed therein. In example embodiments, in the event the voltage detector 119 detects a sufficient voltage drop or increase across the resister 117, the signal generator/transmitter 120 may send out the signal 152. In example embodiments, the signal generator/transmitter 120 may be provided its own power supply 122**, which may be, but is not required to be, a battery.

The specific embodiments of FIGS. 2B and 2C may be used to detect urine. For example, if the insulating materials 113* and 113** become soaked in urine, the electrolytes in the urine may allow for current to travel between the first electrodes 111*, 111** and the second electrodes 112* and 112** thus activating the signal generator/transmitters 120* and 120** so that the signal generator/transmitters 120* and 120** may generate and transmit a signal (for example, a wireless signal) which may have a specific ID code embedded therein. In example embodiments, the specific ID code may correspond to the sensor 100* and 100** which transmitted the signal.

When the circuit is open, that means the insulating material 113* is dry and no electric current will flow through the circuit, namely wires 115, 116 and 117. Hence no current flows through the sensor 120*. When the insulating material 113* is wet with an electricity conducting fluid such as urine, but not limited to urine, the electric circuit is closed and an electric current will flow through it. The sensor (or signal generator) can measure this increase in electric current and consequently generate and transmit an appropriate signal.

In addition, optionally, the sensor can be made to measure the rate at which the current (and the line voltage across a resistor) changes, so that slow changes in the insulating properties of 113* caused by a gradual infusion of the conductive liquid such as, but not limited to perspiration, can be ignored. Such slow infusions can be caused by spurious fluids such as perspiration. A sudden (quick) infusion of a conducting fluid such as urine would cause a quicker increase in the current in the circuit, and the sensor could respond to this quick increase and generate and transmit an appropriate signal.

It is understood that the example sensors 100, 100*, and 100** of FIGS. 2A-2C are not intended to limit the invention but instead are only provided as example of sensors usable with example embodiments. Furthermore, although the sensors 100, 100*, and 100* may be configured to sense a body fluid such as urine or blood, the sensors 100, 100*, and 100** may be configured to sense another composition or condition such as, but not limited to, temperature, pressure, smoke, and/or carbon monoxide.

Figure 3:
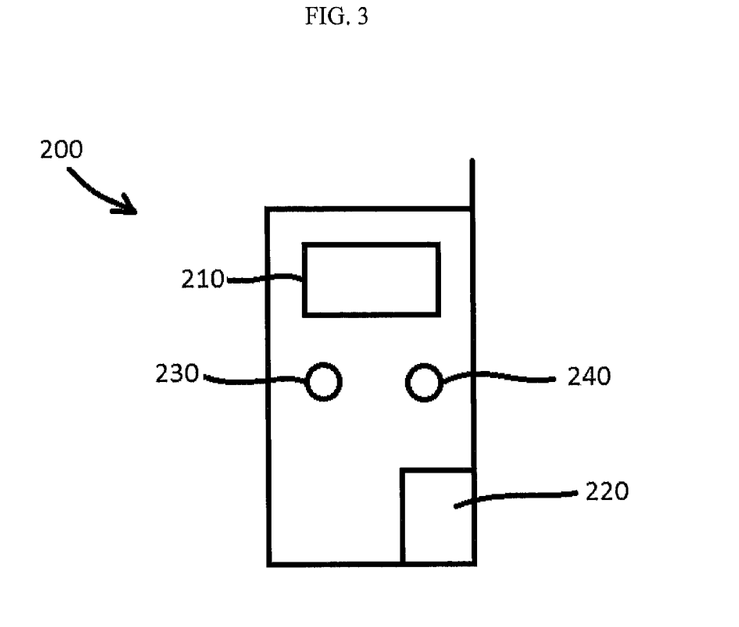
FIG. 3 is a schematic view of a remote in accordance with example embodiments.

FIG. 3 is a view of the remote 200 in accordance with example embodiments. As shown in FIG. 3, the remote 200 may include a signal generator/transmitter 210, a power source 220, an "on" button 230, and an "off" button 240. The power source 220 may be, for example, a battery such as, but not limited to, a three volt battery. In example embodiments the generator/transmitter 210 may be powered by the power source 220. In example embodiments, the signal generator/transmitter 210 may be configured to generate and transmit the second signal 212 having a second identifier therein. In example embodiments, the second identifier associated with the second signal 212 and the third signal 213 generated by the remote 200 may be different from the first identifier associated with the sensor 100. In example embodiments, the second identifier associated with the second signal 212 and the third signal 213 generated by the remote 200 should be a unique signal identifier and should be different from the first signal identifier associated with a signal generated by the sensor 100. In example embodiments the "on" and "off" buttons 230 and 240 may be operatively connected to the signal generator/transmitter 210 so that if either one of the "on" or "off" buttons 230 and 240 are pushed, the signal generator 220 generates a unique and different second signal 212* having the second unique identifier for the "on" button 240 and a different unique third signal 213* for the "off" button 240.

Figure 4A:
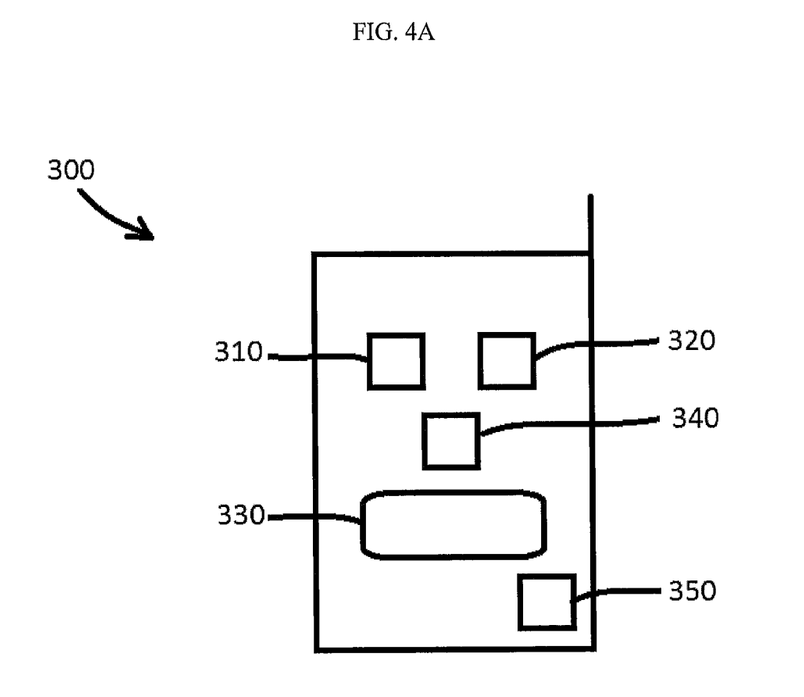
FIG. 4A is a schematic view of a transducer in accordance with example embodiments.
Figure 4B:
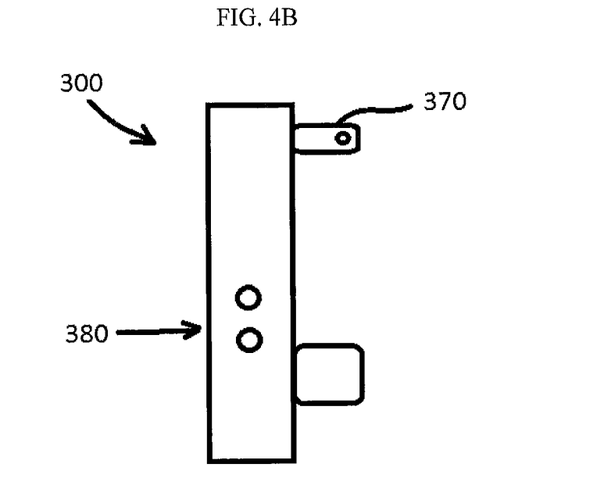
FIG. 4B is a side view of the transducer in accordance with example embodiments.

FIG. 4A is a view of the transceiver 300 in accordance with example embodiments. As shown in FIG. 4, the transceiver 300 may include both a receiver 310 and a transmitter 320. In example embodiments, the receiver 310 and the transmitter 320 may share common circuitry, however, this is not intended to be a limiting feature of example embodiments since the receiver 310 and the transmitter 320 are not required to share common circuitry. Thus, the transceiver 300 may actually function as a receiver-transmitter rather than a transceiver as is well known in the art.

In example embodiments, the transceiver 300 may include a battery 350 which may be used to power the receiver 310 and the transceiver 300. However, example embodiments are not limited thereto. For example, in example embodiments, the transceiver 300 may be further configured (or alternatively configured) with an adapter 370 that may be configured to plug into a conventional wall socket so that conventional AC power may be delivered to the transceiver 300. The AC power is converted to the required DC power and voltage required by the receiver-transmitter. Thus, in example embodiments, the transceiver 300 may be powered either by a battery or by an AC power source.

In example embodiments, the receiver 310 may be configured to receive the signals from the sensor 100 and the remote 200. In example embodiments the transmitter 320 may be configured to transmit a signal that includes the same signal identifier as that generated by the sensor and/or the remote. For example, in example embodiments, in the event the transceiver 300 receives the first signal 152 from the sensor 100 having the first identifier, the transceiver 300 may generate a fourth signal having the first identifier. Similarly, in the event the transceiver 300 receives the second signal 212* from the remote 200 having the second identifier the transceiver 300 may generate a fifth signal having the second identifier therein. If the transceiver 300 receives the signal 213* from the remote 200, it will generate a corresponding sixth signal with the second identifier therein. Thus, in example embodiments, the transceiver 300 may receive a signal from one of, or both of, the sensor 100 and the remote 200 and may retransmit the received signal with its identifiers via the transmitter 320.

In example embodiments, the transceiver 300 may include an alarm 330 which may be configured to generate a signal such as a noise or loud sound. The alarm 330 may, for example, be configured to wake up a sleeping person. In example embodiments, the transceiver 300 may be configured such that the alarm 330 is activated when the transceiver 300 receives a signal from the sensor 100 or deactivated when the activated transceiver 300 receives the signal 213* from the remote 200 (when its "off" button is pressed). In example embodiments the transceiver 300 may also be attached to auxiliary equipment, for example, a bed shaker, another audio alarm, and/or a light. Further, the transceiver 300 may be configured to turn on the auxiliary equipment when it receives a signal from the sensor 100 or deactivate the auxiliary equipment when it receives the signal 213* from the remote 200. Thus, auxiliary equipment may be turned on or off depending on the signal received from one of the sensor 100 and the remote 200.

In example embodiments, the transceiver 300 may have three basic states: an "off" state, a "ready" state, and an "on" state. In the "off" state, the transceiver 300 is essentially nonfunctional, but is ready to receive the "on" signal 212* from the remote 200 and be reset into the "ready" state. In the "ready" state, the transceiver 300 and associated alarms, are ready to receive a signal from the sensor 100 or the signal 213* from the remote 200. In the "on" state the alarm 330, and other auxiliary alarms associated with the transceiver 300 are activated. In example embodiments, the transceiver 300 may switch from the "off" state to the "ready" state by pressing the "on" button of the remote 200. In the alternative, the transceiver 300 may be configured with a switch 340, for example, a main power switch (MPS) which may be associated with the transceiver 300. In example embodiments, the switch 340, when pressed may switch the transceiver 300 between the "ready" and "off" states.

In example embodiments the remote 200 may be configured to affect the transceiver 300 and can switch the transceiver from the "off" state to the "ready" state by pressing the "on" button 230, from the "on" state to the "ready" state by pressing the "off" button 240, and from the "ready" state to the "off" state by pressing the "off" button 240 again.

Figure 5:
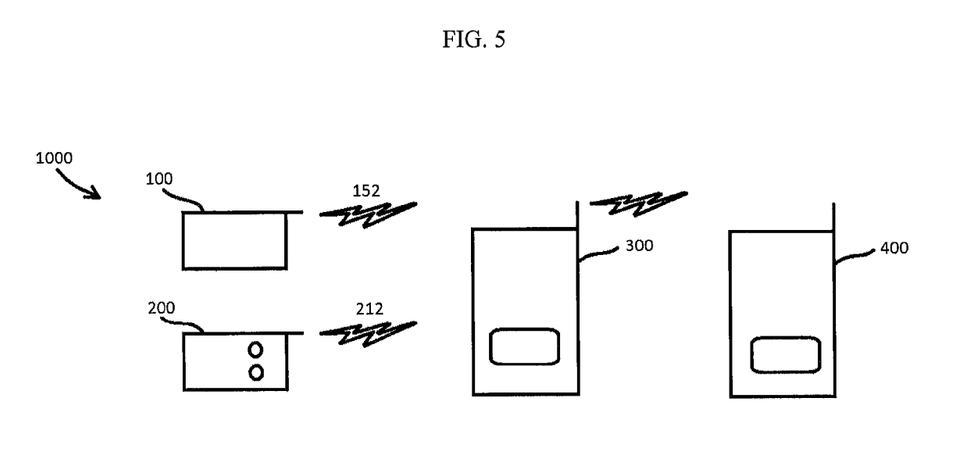
FIG. 5 is a view of a system in accordance with example embodiments.

FIG. 5 is a view of the system 1000 further including a second transceiver 400. In example embodiments the second transceiver 400 may be substantially the same as the first transceiver 300, thus a detailed description thereof is omitted for the sake of brevity.

As indicated above, the transceiver 300 includes each of a receiver 310 and a transmitter 320. In example embodiments, the receiver 310 may be configured to receive signals from each of the sensor 100 and the remote 200. For example, in example embodiments, the sensor 100 may send a signal having the first signal identifier. This signal may be received by the first transceiver 300 causing the alarm 330 of the first transceiver 300 to generate a signal (such as a noise, a vibration, and/or a light). In example embodiments, the first transceiver 300 will retransmit the signal to the second transceiver 400 to cause the second transceiver to receive this signal and for 400 to generate an alarm (such as a noise, a vibration, and/or a light) and retransmit the signal for reception by additional tranceivers (which may be substantially identical to the first transceiver 300). Thus, in example embodiments, because each of the first and second transceivers 300 and 400 receive a substantially same signal at substantially a same time, the first and second transceivers 300 and 400 may each generate an alarm (for example a noise, a vibration, and/or a light) at substantially a same time. Similarly, a user pressing the "off" button 240 of remote 200 may send a signal from the remote 200 to the first transceiver 300 to turn off the first transceiver's alarm 330 and the first transceiver 300 may retransmit the signal to the second transceiver 400 to turn off the second transceiver's alarm. Similar yet, in the event each of the first and second transceivers 300 and 400 are in an "off" state, the transceivers 300 and 400 may each be switched to an "ready" state by pressing the "on" button 230 of the remote to transmit a second signal to the first transceiver 300 and having the first transceiver retransmit the signal to the second transceiver 400.

As mentioned above, the signals sent from the sensor 100 and the remote 200 may include unique signal identifiers. In example embodiments, the transceiver 300 (or additional transceivers) may be set to synchronize its reception and transmission only to signals generated by the sensor 100 and the remote 200. Thus, the transceiver 300 (or additional transceivers that cooperate with the transceiver 300) will receive and retransmit signals that carry the aforementioned unique signal identifiers. This allows a practically unlimited number of sensors, remotes and related transceivers to operate in a same physical or wireless vicinity, but each transceiver will only respond to a signal with the pre-set ID code, corresponding to a particular and unique sensor and remote.

As each transceiver in a system responds to only the uniquely coded transmissions from a sensor and remote to which it is synchronized, and then retransmits that received signal, several transceivers, of which each must be within the signal reception distance of its closest transceiver's transmission, can be networked or even "daisy-chained" to be an effective network of transceivers all of which respond to a particular sensor and/or remote transmission at essentially the same instant in time. All such transceivers in a network system must be synchronized with the particular sensor and remote used in that network system.

Figure 6:
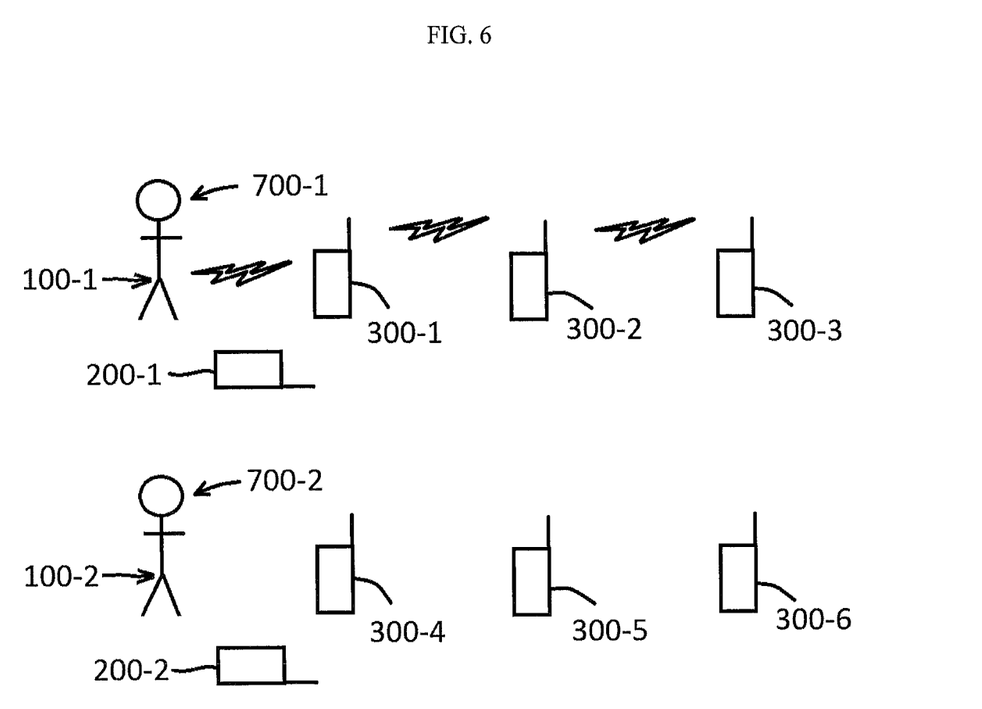
FIG. 6 is a view of a system in accordance with example embodiments.

FIG. 6 is a view of a specific nonlimiting implementation of the invention in accordance with example embodiments. As shown in FIG. 6, a first person 700-1 and a second person 700-2 may be fitted with a first sensor 100-1 and a second sensor 100-2. In example embodiment, the first and second sensors 100-1 and 100-2 may be attached to undergarments of the first and second person 700-1 and 700-2 and may be configured to sense a presence of urine. For example, in example embodiments, the first and second sensors 100-1 and 100-2 may be substantially identical to the previously described sensor 100 and the first and second sensors 100-1 and 100-2 may be attached to the first and second person's undergarments by clipping and or pinning the sensors 100-1 and 100-2 to the person's undergarments. On the other hand, a portion of the person's undergarments may be sandwiched between the first and second electrodes of the first and second sensor 100-1 and 100-2.

Referring again to FIG. 6, the presence of a first remote 200-1, a second remote 200-2, and a plurality of transceivers 300-1, 300-2, 300-3, 300-4, 300-5, and 300-6 is shown. In example embodiments, the first and second remotes 200-1 and 200-2 may be substantially identical to the previously described remote 200 and the plurality of transceivers 300-1, 300-2, 300-3, 300-4, 300-5, and 300-6 may be substantially identical to the transceiver 300.

In example embodiments, the first sensor 100-1, the first remote 200-1 and the first, second, and third transceivers 300-1, 300-2, and 300-3 may be synchronized. That is, in example embodiments, the first, second, and third transceivers 300-1, 300-2, and 300-3 may be configured to only respond to signals sent by the first sensor 100-1 and the first remote 200-1. This may be accomplished by configuring the first, second, and third transceivers 300-1, 300-2, and 300-3 to respond to signals that include the unique signal identifiers associated with the first sensor 100-1 and the first remote 200-1. Similarly, the second sensor 100-2 and the second remote 200-2 and the fourth, fifth, and sixth transceivers 300-4, 300-5, and 300-6 may be synchronized. That is, in example embodiments, the fourth, fifth, and sixth transceivers 300-4, 300-5, and 300-6 may be configured to only respond to signals sent by the second sensor 100-2 and the second remote 200-2. This may be accomplished by configuring the fourth, fifth, and sixth transceivers 300-4, 300-5, and 300-6 to respond to signals that include the unique signal identifiers associated with the second sensor 100-2 and the second remote 200-2.

In example embodiments, because the first, second, and third transceivers 300-1, 300-2, and 300-3 are configured to respond to signals generated by the first sensor 100-1 and the first remote 200-1, they will not respond to a signal or retransmit a signal that is received from the second sensor 100-2 or the second remote 200-2. Similarly, because the fourth, fifth, and sixth transceivers 300-4, 300-5, and 300-6 are configured to respond to signals generated by the second sensor 100-2 and the second remote 200-2, they will not respond to a signal or retransmit a signal that is received from the first sensor 100-1 or the first remote 200-1 For example, if the first sensor 100-1 detects a presence of urine the first sensor 100-1 will send a signal having the first unique identifier to the transceivers. In the event the first transceiver 300-1 and the fourth transceiver 300-4 are in the range of the first signal, only the first transceiver 300-1 will activate its alarm and retransmit the signal since the fourth transceiver 300-4 is configured to respond to signals having a different identifier. Similarly, if a user operates the first remote 200-1 by, for example, pressing the off button, the first remote 200-1 will send a signal having another unique identifier to the transceivers. In the event the first transceiver 300-1 and the fourth transceiver 300-4 are in the range of the signal sent by the first remote 200-1, only the first transceiver 300-1 will respond (for example, by shutting down an alarm) and retransmit the signal since the fourth transceiver 300-4 is configured to respond to signals having a different identifier.

The use of unique identifiers provides several advantages. For example, in the event the first person 700-1 and the second person 700-2 are in relatively close proximity to one another (for example, sharing the same room, or in adjacent rooms, or in adjacent apartments in an apartment building), synchronizing their respective sensors and remotes to their respective transducers will help prevent the first person 700-1 from activating or deactivating the transceivers (and their associated alarms) associated with the second person 700-2.

In example embodiments, it is possible that some transceivers may not be in range of a sensor sending out a signal. However, because at least one transceiver will be in the range of the sensor, then at least one transceiver may send a signal which may be received by the one or more of the other transceivers outside of the direct transmission range of the sensor. Thus, in example embodiments, several transceivers may be daisy-chained in order to expand the overall range of the system. For example, in a multilevel house, a child wearing a sensor may have an upstairs bedroom whereas a monitoring parent may be in a basement area. In this particular example, the basement may be out of range of the sensor that is in the child's room. However, in example embodiments, an intermediate transceiver, which is within range of both the sensor and the basement may be used to transmit a signal from the child's sensor to a transceiver arranged in the basement.

Example embodiments of the invention have been described in an illustrative manner. It is to be understood that the terminology that has been used is intended to be in the nature of words of description rather than of limitation. Many modifications and variations of example embodiments are possible in light of the above teachings. Therefore, within the scope of the appended claims, the present invention may be practiced otherwise than as specifically described.

Embellishments can be added to the parts or items that constitute a system so as to make the setup and operation more convenient. For example, but not necessarily restricted to such, a physical button on every transceiver can be manually depressed to switch on the built-in audio alarm so that it's volume can be changed to a suitable level for the user. As another example, the sensor can be made to sense wetness (possibly urine) in more than one manner, using different schemes for configuring the sensor and the wetness-absorbing insulator between the appropriate two electrodes.

What we claim is:

1. A detection system comprising:
a sensor configured to sense a condition and send a first signal when the condition is sensed, the first signal including a first unique identifier;
a remote configured to send a second signal and a third signal, the second and third signals including a second unique identifier;
a first transceiver configured to receive and retransmit the first, second and third signals, wherein the first transceiver, when in a "ready" state, is configured to activate a first alarm when the first signal is received (turn "on") and deactivate the first alarm when the third ("off") signal is received (turn "off") and place the transceiver in the "ready" state, whereby receiving the third signal again changes the transceiver from the "ready" state to an "off" state, in which state it can not receive the first signal from the sensor to activate the alarm and whereby receiving the second signal ("on") from the remote changes the transceiver from the "off" state to the "ready" state wherein a subsequent reception of the first signal from the sensor activates the first alarm associated with the transceiver; and
a second transceiver configured to receive the retransmitted first, second, and third signals from the first transceiver, wherein the second transceiver is configured to activate a second alarm when it receives the first retransmitted signal and deactivate the second alarm when it receives the third retransmitted signal.

2. The system of claim 1, wherein the first transceiver is configured to be in at least one of three states.

3. The system of claim 2, wherein the first state is the "off" state, the second state is the "ready" state, and the third state is an "on" state.

4. The system of claim 1, wherein the condition is a presence of a body fluid or any substance that effectively closes an open electric circuit.

5. The system of claim 4, wherein the body fluid is one of blood and urine or any other substance that closes the open circuit.

6. The system of claim 1, wherein the remote includes an on button and an off button.

7. The system of claim 6, wherein the first transceiver is configured so that when the off button of the remote is pushed the alarm associated with the first transceiver is deactivated (from an "on" state to the "ready" state).

8. The system of claim 6, wherein the first transceiver is configured so that when the off button of the remote is pushed the first transceiver changes from the ready state to the "off" state.

9. The system of claim 7, wherein the remote is configured so that when the on button is pushed the first transceiver changes from the "off" state to the ready state.

\* \* \* \* \*